United States Patent [19]

Zuesse

[11] 4,161,946
[45] Jul. 24, 1979

[54] SUPPORT FOR MAINTAINING HEAD IN UPRIGHT POSITION

[76] Inventor: Lance E. Zuesse, New York, N.Y.

[21] Appl. No.: 874,580

[22] Filed: Feb. 2, 1978

Related U.S. Application Data

[63] Continuation of Ser. No. 752,138, Dec. 20, 1976, abandoned, which is a continuation-in-part of Ser. No. 675,929, Apr. 12, 1976, abandoned.

[51] Int. Cl.² .............................................. A61H 1/02
[52] U.S. Cl. .................................... 128/75; 128/87 B; 128/DIG. 20
[58] Field of Search .................... 128/75, 76 R, 87 R, 128/87 B, 89 A, DIG. 20, DIG. 23; 2/2, 3, 245

[56] References Cited

U.S. PATENT DOCUMENTS

| 678,417 | 7/1901 | Muller | 128/DIG. 23 |
|---|---|---|---|
| 2,672,146 | 3/1954 | Touson | 128/DIG. 23 |
| 3,724,452 | 4/1973 | Nitschke | 128/75 |
| 3,765,412 | 10/1973 | Ommaya et al. | 128/DIG. 20 |
| 3,818,509 | 6/1974 | Romo et al. | 2/3 R |
| 3,957,040 | 5/1976 | Calabrese | 128/75 |

Primary Examiner—John D. Yasko

[57] ABSTRACT

A support for maintaining the head in an upright position, as, for example, while resting or sleeping upright in a seat with a back rest. The support includes a forehead-engagement means to resist forward movement of the head. Forehead pressure against this means is transmitted to a nape-of-the-neck-engagement means, which is thereby pressed inwardly upon the rear of the neck. This pressure is then further transmitted by way of a chest-engagement means inwardly upon the sternum. Since the nape of the neck cannot move forward, and the sternum cannot move inward, falling forward of the forehead is precluded.

Various ancillary support means can be added to supplement the basic head support. Thus, in some embodiments, the nape-engagement means is extended upwardly to provide an occipital support section which engages the rear of the head and is extended downwardly to form a posterior support section for engaging the upper rear portion of the wearer's back. A shoulder-engaging frame fits across the wearer's shoulders and connects to the posterior support, in one embodiment, lateral supports extend from the shoulder-engaging frame to engage the sides of the wearer's head, and a chin support rises from the chest-engagement means.

The complete support can be formed of rigid sections coupled together, or it can be formed of flexible material having an integral air chamber to provide a semi-rigid support. All versions of this head support depend on the basic principle of resisting forward movement of the head by the forehead-engagement means or headband transmitting this pressure to the nape and to the sternum, neither of which moves.

18 Claims, 3 Drawing Figures

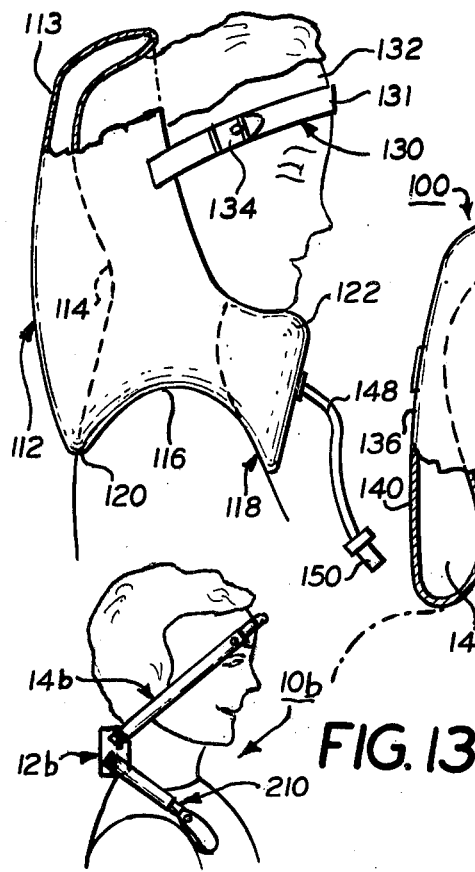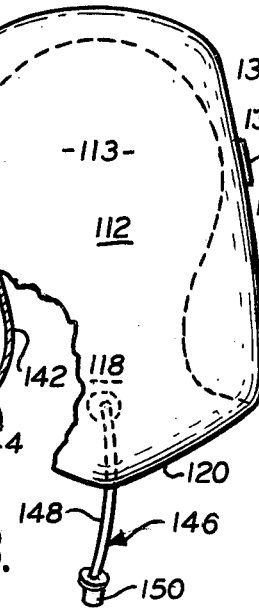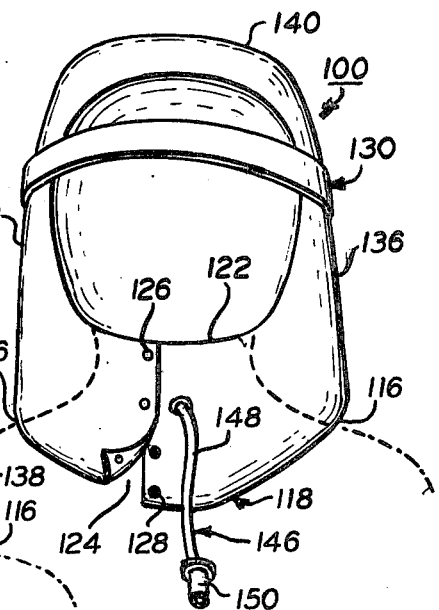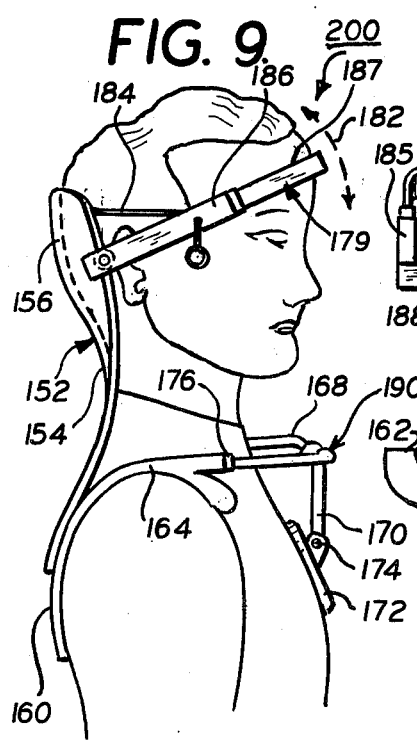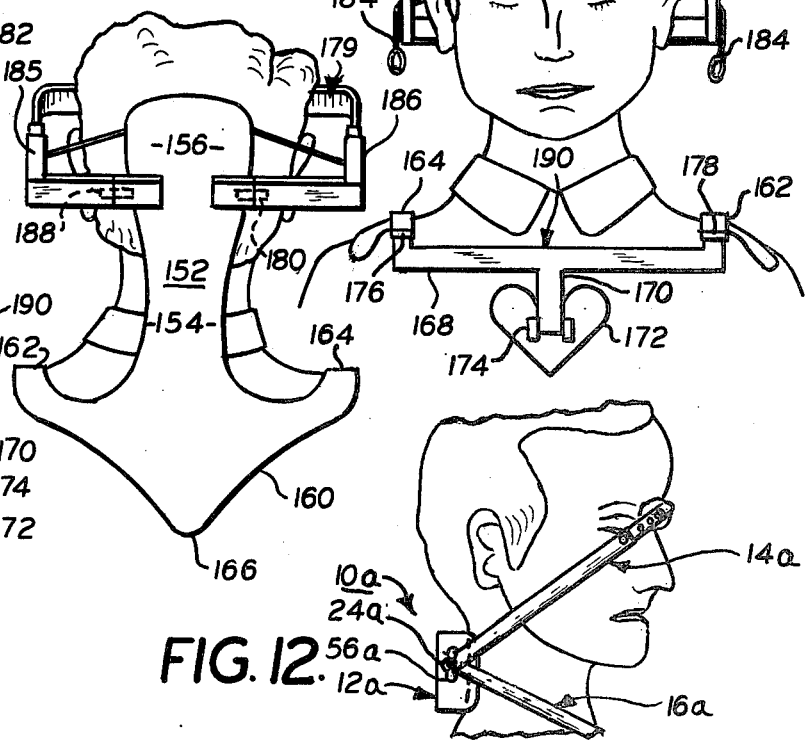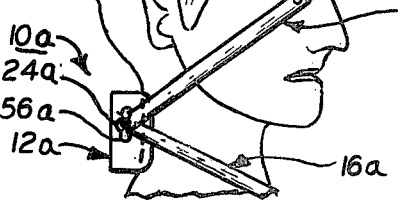

SUPPORT FOR MAINTAINING HEAD IN UPRIGHT POSITION

BACKGROUND OF THE INVENTION

This application is a continuation of Ser. No. 752,138 filed Dec. 20, 1976, now abandoned; which is a continuation-in-part of Ser. No. 675,929, filed Apr. 12, 1976, now abandoned, entitled: Head Support for Sleeping in Upright Position.

This invention relates to head supports and more particularly to a support intended for use in supporting the head for resting or sleeping in an upright position.

Long rides in cars, buses, trains, ship sleeperettes and planes have become a regular routine. The length of travel time and cramped conditions of the seating often require the traveler to sleep in an upright position. Many of the transportation means try to facilitate such sleeping by providing reclining chairs. However, both with and without such reclining chairs, sleeping in an upright position is awkward, uncomfortable and totally unrelaxing.

The main factor which inhibits sleeping in an upright position is that the head tends to slope or fall as the traveler goes to sleep. Each time the head tilts or droops, this tends to reawaken the traveler and prevent his truly falling asleep. Even if the traveler manages to fall asleep, the tilting of the head downward, to the side, or backward, frequently gives the traveler a stiff neck and a restless and uncomfortable feeling.

At frequent occasions not only does the traveler wish to fall asleep, but many times he merely wishes to rest his eyes and head for a short period. Also, the individual who is not traveling but only sitting up either at work or in his home and cannot conveniently find a place to lie down to rest, may want to take a brief resting period. However, even then, because the head tends to droop and fall forward, backward or to the side, such resting is inconvenient and uncomfortable.

There presently exist many types of head supports and cervical braces, for maintaining the head and nect portions in erect position and preventing movement of various parts of the head and neck. In most cases, the purpose of such supports and braces is to immobilize the head with respect to the neck portion, and generally such braces are utilized for therapeutic purposes in order to give the cervical nerves and muscles an opportunity to heal.

While the prior art devices have served to immobilize portions of the head and neck structure and maintain portions of the head in upright position, they have failed to provide proper and adequate support for the head while sleeping or resting in a sitting position. The basic reason is that such prior art devices have failed to address themselves to the movement of the head during the course of sleep. Since most of the prior art devices are for orthopedic and therapeutic uses, they generally address themselves to the problem of preventing movements of the awake head pivoted about the neck. Also, all of them prevent the chin from moving downward toward the chest, and all prior art devices function by supporting the chin and maintaining traction for the cervical column. This is too uncomfortable for rest or sleep.

When falling asleep, the most frequent movement of the head is a forward movement, with the middle part of the nape at the back of the neck remaining quite stationary. Additionally, sideward movements occur during sleep. Furthermore, for a comfortable sleep, it is required that there be as much freedom as possible for the jaw to open and close. Otherwise, with too much pressure upward againt the jaw, the pressure will be transferred to the teeth and will cause an uncomfortable feeling under the gums during sleep. Unlike prior art devices which support the awake head, a device capable of maintaining a sleeping head in an erect position cannot depend at all upon the functioning of the muscles in the neck, since these are entirely relaxed during sleep. Also, pressure against the chin and teeth must be minimized for optimal comfort, to permit relaxed sleep. No prior art device meets both requirements.

SUMMARY OF THE INVENTION

It is accordingly an object of the present invention to provide a support for the head while resting or sleeping in an upright position, which will resist forward and lateral movements of the head, yet provide as much freedom for jaw movement as possible, thereby permitting the wearer to sleep as comfortably as possible when seated in an upright position.

Yet a further object of the present invention is to provide such a support which can be adjusted to fit different wearers.

Still another object of the present invention is to provide such a support which can be simply and easily installed on the wearer and which can be collapsed conveniently for greater portability.

A further object of the present invention is to provide such a support which is inexpensive to manufacture, and which can be readily mass produced.

These objects are achieved in the present invention, wherein the support for maintaining the wearer's head in an upright position is based on the concept of using the relatively unmoving nape of the neck as the focal base of support, causing it to serve as a fulcrum to transmit and translate forward pressure of the forehead into inward pressure upon the sternum.

In its simplest form, the head support of this invention includes a support means engaging and encompassing the nape of the neck. An adjustable forehead-engagement means or headband extends forwardly and upwardly from the nape-engagement means for positioning around the wearer's forehead. A chest-engagement means extends forwardly and downwardly from the nape-engagement means to engage the wearer's sternum. In this form, the head support is constructed of separate rigid parts, with the forehead-engagement means and the chest-engagement means pivotally connected to the nape-engagement means, and is adjustable to fit various sizes of the wearer and collapsible for convenience.

Other embodiments of the present invention include additional subsidiary supports, all of which are devised to enhance or supplement the effectiveness of the head support. Each of these ancillary support means exerts a restraining influence in addition to that of the above mentioned basic forehead-nape-sternum structure. In these embodiments, the nape-engagement means incorporates an upwardly extending occipital support means for engaging and retaining the rear of the head, and a downwardly extending posterior support means adapted to be placed on the wearer's back, which together function to resist backward movement of the head. In addition, a shoulder-engaging-frame means, adapted to fit over the wearer's shoulders, is connected to the posterior support means.

In one embodiment of the invention, there are further included lateral head support sections, and an optional chin support section. In this embodiment, all of the support sections, with the exception of the adjustable headband, are formed of an integral construction having an outer wall enclosing the wearer's neck, parts of his head, upper back and upper chest, and an inner wall conforming to the shape of the wearer's neck and parts of his head, upper back and upper chest. An air chamber is formed between the two walls which can be inflated, thereby forming a semi-rigid support.

In another embodiment of the invention, separate sections are utilized, all of which are rigid. The headband extends around the forehead from an occipital support means which extends upward from a posterior support means. Two arms forming the shoulder-engaging-frame means merge with this posterior support. An adjustably detachable U-shaped member serving as the upper part of the chest-engagement means connects to the front of the two shoulder arms that constitute the shoulder-engagement-frame means, and there extends downwardly from the middle of this U-shaped member a bar connecting to a pivotal chest plate which engages the sternum. The bar and chest plate comprise together the lower portion of the chest-engagement means.

BRIEF DESCRIPTION OF THE DRAWINGS

Other objects and many of the attendant advantages of the present invention will be readily appreciated and better understood by reference to the following detailed description when considered in connection with the accompanying drawing in which like reference numerals designate like parts throughout the figures thereof and wherein:

FIG. 6 is a side view of an inflatable embodiment of the invention in use and is shown partially broken away;

FIG. 7 is a front view of the inflatable embodiment;

FIG. 8 is a rear view of the inflatable embodiment and shown partly broken away and in section;

FIG. 9 is a side view of another embodiment of the present invention in use;

FIG. 10 is a front view of the device shown in FIG. 9;

FIG. 11 is a rear view of the support of FIGS. 9 and 10; and

FIGS. 12 and 13 are partial side views of still other embodiments of the heat support.

DESCRIPTION OF THE PREFERRED EMBODIMENTS

Figure 1:
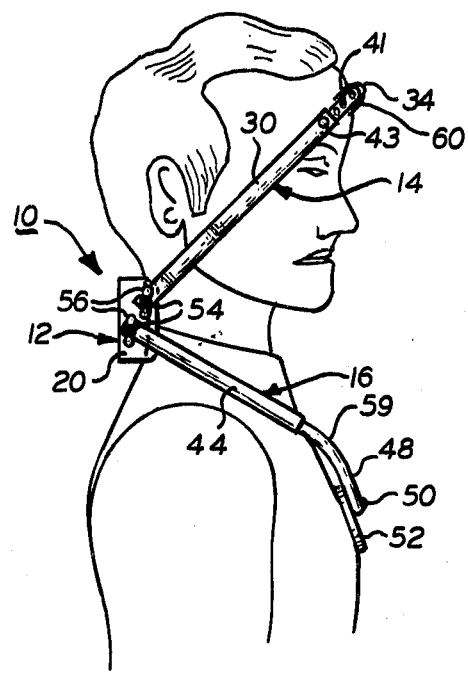
FIG. 1 is a side view of a basic illustrative embodiment of this invention in use.
Figure 2:
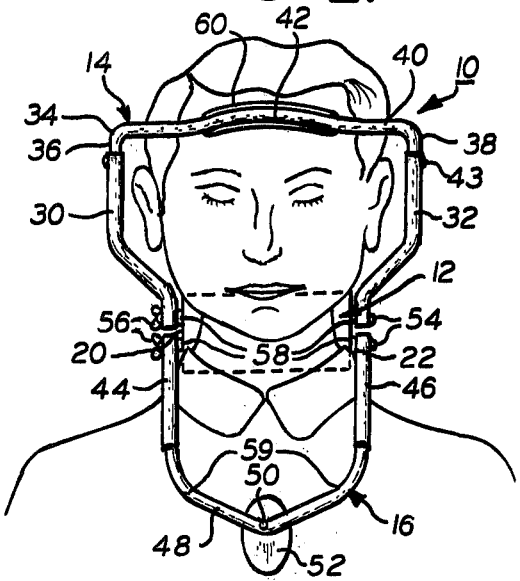
FIG. 2 is a front view of the device shown in FIG. 1.
Figure 3:
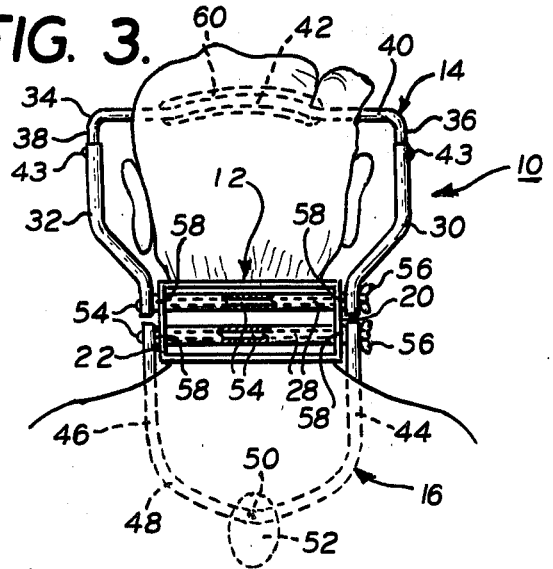
FIG. 3 is a rear view thereof.

The invention in its fundamental concept utilizes forehead-, nape-, and sternum-engagement means. Specifically, a nape-engaging means serves as a fulcrum to transmit forward pressure of the forehead upon the forehead-engaging means downward to become inward pressure against the sternum by way of the sternum-engaging means. Both forehead- and sternum-engaging means are rigidly but adjustably connected to the nape-engaging means. Some embodiments include a nape-engaging means which is expanded upwardly to form an occipital support section for engaging the rear of the head, and expanded downwardly to form a posterior support section for engaging the upper back between the shoulder blades; and a shoulder-engaging frame which extends forward from the posterior support section so as to fit over the wearer's shoulders. Still another embodiment adds lateral support means extending upwardly from the shoulder-engaging frame to engage the sides of the wearer's head, chin support means emerging upwardly from the chest-engaging means; and the head support can be inflatable by the provision of an integral air chamber.

Referring now to FIGS. 1–5, a first embodiment is described which illustrates the basic concept of the invention. In this version, all components are made of rigid materials chosen for minimum weight and bulk consistent with adequate strength. The head support, generally designated as 10, includes nape-engagement means 12, forehead-engagement means 14, and chest-engagement means 16.

Nape-engagement means 12 is shown as a generally rectilinear box-like structure with the medial portion 18 of its front face contoured for close engagement with the nape of the neck of the wearer. End walls 20 and 22 of nape-engagement means 12 are both shown with two holes 24 and 26 for pivotally mounting forehead-engagement means 14 and chest-engagement means 16 respectively. Holes 24 and 26 are shown disposed in staggered relationship to permit head support 10 to be collapsed into the position of FIG. 5. Nape-engagement means 12 may be suitably strengthened by braces 28, shown here as tubular, or in other conventional ways (not shown), such as forming means 12 out of solid structural foam.

Forehead-engagement means 14 includes face-framing adjustment means 30 and 32 of tubular or other light rigid construction, which assist in length-adjustment of means 14 to fit diverse heads, and each of which is pivotally mounted at its lower end to one end of means 12 at an opening 24. Forehead-restraining means 34 is shown here as a generally U-shaped bar fashioned so that its sides 36 and 38 fit telescopically and adjustably into the upper tubular portions of adjustment means 30 and 32 respectively. Connecting portion 40 of forehead-restraining means 34 is shown centrally curved at 42 for fitting engagement with the wearer's forehead. Pad 60 is shown mounted on forehead-restraining means 34 at 42. Means 41,43 for positioning forehead-restraining means 34 within adjustment means 30 and 32 are provided.

Chest-engagement means 16 has adjustment means, shown as two straight tubes 44 and 46, each pivotally mounted on one end of nape-engagement means 12 at an opening 26, which permit length-adjustment of means 16. Shown telescopically fitting and held within the lower ends of elements 44 and 46 is U-shaped member 48, illustrated here as having compound curvature at 59. Chest-engaging element 52 is pivotally mounted at curvature-apex 50, and is worn in firm engagement with the wearer's sternum.

Both means 14 and 16 are shown mounted on nape-engagement means 12, each with a bolt 54 extending through means 12 and each held by a wing nut 56, with spacers 58 provided at both ends.

In operating head support 10, forehead-engagement means 14 is moved upwardly, and U-shaped member 48, with chest-engaging element 52 attached, is removed.

Nape-engagement means 12 is placed against the nape of the neck, with adjustment means 44 and 46 loosely held by lower wing nut 56 so that U-shaped member 43 can be now slipped back into place, adjusted so that chest-engaging element 52 firmly contacts the sternum, and lower wing nut 56 at pivot point 26 is tightened. Forehead-engagement means 14 is now swung into place, adjusted to the proper length so that bar 34 is in firm engagement with the forehead, and secured in the desired position by tightening upper wing nut 56 at pivot point 24.

The wing nuts 56, bolts 54, and spacers 58 together comprise retention means to adjust the angular fit of forehead-engagement means 14 and chest-engagement means 16.

During sleep, as the head tends to move forward, the nape of the neck does not shift forward but remains stationary. The forehead presses forward against 42; 18 presses forward against the nape; and 52 presses inward against the sternum. Nape-engagement means 12 serves as a fulcrum which transfers the pressure of the falling forehead against bar 34 ultimately to chest-engaging element 52, where the sternum resists the falling forward of the sleeping head. Lateral head movement is also discouraged by the fitting curvatures of nape-engagement means 12 at 18 and forehead bar 34 at 42, both of which may be suitably padded for greater wearing comfort, as may be chest-engaging element 52.

Referring now to FIGS. 6-8, another embodiment of the broad forehead-nape-sternum concept is described as an inflatable model. This embodiment is formed as a single integral construction having an outer wall which forms a shell, shown shaped as a neck and partial head, back and chest cover, and an inner wall which conforms to the shape of these parts of the body. An air chamber therebetween can be filled with air to provide a semi-rigid enclosure.

The support, 100, is shown with expanded nape-engagement means 112, which extends upwardly to form occipital support section 113 located along the back of the head, and downwardly to form posterior support section 120 on the wearer's back. Specifically, inner wall 114 is positioned at and beneath the occiput portion of the head, along the neck and down the upper back between the shoulders. The shoulder-engaging-frame section 116 fits over the shoulders and connects to chest-engagement means 118, which is placed over the wearer's chest, and specifically engages the region around the sternum.

Chest-engagement means 118 contains an upwardly extending chin-support means 122, which is adapted to be placed beneath the wearer's chin so as to supplement the head-supporting effectiveness of this semi-rigid embodiment. Chest-engagement means 118 contains a slit portion 124 in the center thereof and includes fastening means 126,128 on either side of the slit. Such fastening means are shown as snaps; however, other types of fasteners including Velcro fasteners, zippers, etc. may be utilized.

A forehead-engagement means 130 is connected to nape-engagement means 112 and is adapted to be positioned around the wearer's forehead 132. An adjustment means, such as strap-and-buckle 134, plus a forehead-restraining means 131, are included in the forehead-engagement means.

Head support 100 as shown, with the exception of forehead-engagement means 130, is formed of a unitary integral structure containing an outer wall 140 which forms a neck and partially head, upper-back and upper-chest enclosure, and an inner wall 142 which conforms substantially to the shape of these body-parts. An air chamber means 144 is formed between the outer and inner walls 140,142. An inflating means 146 is connected to air chamber means 144. The inflating means 146 includes a tube 148 and a nozzle 150, and may be used to fill air chamber means 144 by mouth or air pump. Other types of inflating devices may also be utilized, including a pump and valve unit of the sphymomanometric type.

In operating the support of FIGS. 6-8, heretofore described, the fastening means 126,128 would be opened and the slit portion 124 spread to permit the support to be placed around the wearer's head and neck. The fasteners are then closed. The air chamber means is blown up until the inner wall snugly fits around the head and neck and a semi-rigid structure is formed. It is noted that the air inflation of this embodiment serves as adjustment means, and urges the respective means into supportive engagement with the neck, head, upper back, upper chest, shoulders and chin. Next, the forehead-engagement means 130 is placed over the forehead and adjusted to the proper size. The device then restrains movements of the head in various directions, transferring all forces through nape-engagement means 112 mounted on the stationary nape of the neck. Should the head move forward, forehead-restraining means 131 would resist the movement and would transfer the forward force of the forehead to the main body of the support, which will be squeezed downwardly and inwardly. Specifically, chest-engagement means 118 would be pressed inwardly and squeezed against the chest. This would restrain the head from forward movement. Backward movement would cause the head to push against the occipital support section 113 which would transmit the force downwardly, causing the posterior support section 120 to be squeezed against the back, thus deterring backward movement of the rear of the head. Similarly, sideward movement of the head would press against the lateral support means 136,138, transmitting such force down to movement. The chin-support means 122 also aids in restraining the forward and downward movement of the head. However, most of the forward pressure would be applied against forehead-restraining means 131 and, therefore, little if any pressure would be placed directly from the chin onto chin-support means 122. In fact, there will be flexibility between the chin and chin support thereby providing freedom for the jaw to open and close during the course of sleep, and preventing the placement of excess pressure on the teeth during sleep.

It is therefore noted that utilizing the supports heretofore described, the head is maintained in an upright position, restraining forward, backward and lateral movements.

Modification can be made in the inflatable version of FIGS. 6-8 without departing from the spirit or essence of this embodiment. For example, it may be anchored to the rib cage, as by a strap or belt construction extending down from and attaching to the bottom of posterior support section 120, and then extending around the rib cage and being fastened with a buckle. On the the other hand, portions of the device may be omitted, as for example the chin support.

Both walls of head support 100 can be made flexible, or, alternatively, outer wall 140 can be made rigid and only inner wall 142 made flexible.

Referring now to FIGS. 9–11, another embodiment of this invention referenced generally as 200 will be described wherein components are used, and no inflating is necessary. Nape-engagement means 152 is inwardly curved at 154 to conform to the curvature of the nape of the neck, extends upwardly and is curved and positioned at 156 to hold the occiput and the rear portion of the head, and extends downwardly to the posterior support section 160.

The shoulder-engaging-frame means includes the shoulder arms 162,164 which are placed around the top of the shoulders. Posterior support means 160 merges the back of the two arms 162,164 together with nape-engagement means 152 and forms a substantially triangular back section which ends in a downward apex 166 positioned against the upper back of the wearer.

Connected to the front shoulder arms 162,164 is U-shaped member 168, shown extending downward at arm 170. Chest-engaging element 172 is pivoted to arm 170 by means of the pivot 174. U-shaped member 168 is coupled to shoulder arms 162,164 by adjustment means 176,178, permitting the device to be put on and taken off, and also providing a means whereby the distance which bar 168 extends from arms 162,164 can be adapted to fit different sizes of wearer's chests. Chest-engaging element 172 and U-shaped member 168, with its extending arm 170, and adjustment means 176,178, together constitute the chest-engagement means 190.

Pivotally connected to nape-engagement means 152 is forehead-engagement means 179. By use of pivots 188,180, the headband can move up and down, as shown by arrow 182. Retention means 184 between nape-engagement means 152 and forehead-engagement means 179, shown as a connecting cord but possibly being otherwise, holds forehead-restraining means 187, shown here as a generally U-shaped bar, in the desired position against the forehead. Forehead-engagement means 179 includes forehead-restraining means 187, with its central portion shown shaped to fit the forehead's contour and padded, and also includes adjustment means 185,186, shown as telescoping arrangements permitting the legs of forehead-restraining means 187 to be moved in and out, thereby accomodating various head sizes. Retention means 184 is shown as a cord arrangement similar to that conventionally used in venetian blinds, which permits adjusting the length of the cords as desired, and at the same time provides easy manipulation.

In operating device 200 shown in FIGS. 9–11, the forehead-engagement means 179 is moved upwardly, and U-shaped member 168 is removed. Shoulder arms 162,164 are then placed over the wearer's shoulders with nape-engagement means 152 placed against the back of the head. The two legs of U-shaped member 163 are then inserted into adjustment means 176,178 and positioned so that chest-engaging element 172 lies comfortably on the sternum. Forehead-restraining means 187 is then lowered over the forehead and the length of forehead-engagement means 179 is then adjusted by adjustment means 185,186 so that 187 is directly in front of the forehead. Retention means 184 is then set to maintain means 187 in the desired position.

As with the previously described embodiments, the device of FIGS. 9–11 owes its effectiveness to the fulcrum action of the nape-engagement means 152, working in conjunction with forehead-engagement means 179, and chest-engagement means 190. The sleeping forehead will fall against forehead-engagement means 179 causing pressure to be transferred through nape-engagement means 152 to chest-engaging element 172 of chest-engagement means 190, which applies an inward pressure against the nape and sternum, both of which resist the falling forward of the sleeping head. At the same time, backward movement of the sleeping head is resisted by using the downward apex of posterior support 166 as an ultimate pressure point. When the head begins backward movement, the rearmost part of the skull moves downwardly. This creates a downward pressure against the occipital support section 156 of nape-engagement means 152. The downward pressure is resisted both at downward apex 166 and at shoulder arms 162,164 which cross over from the rear to the front. Lateral movement is deterred by the curvatures of occipital support 156 and forehead-restraining means 187, which transmit the force of any sideward movement to the offsetting resistance of shoulder arms 162,164.

It is noted that of the three embodiments herein described, the two rigid versions use no chin support at all, permitting complete freedom for movement of the chin and jaw; even in the inflatable version, the chin support is secondary, as above described, and optional Extension of the concepts of this invention has been contemplated and is illustrated in FIGS. 12 and 13. In FIG. 12, head support 10a comprises nape-engagement means 12a, bridge-of-the-nose-engagement means 14a, and chest-engagement means 16a. Means 14a and 16a are shown as being pivoted on means 12a at a single pivot point 24a and held in by a single wing nut 56a. Except for the bridge-of-the-nose engagement and the single pivot, the head support 10a shown is completely similar in construction and operation to the embodiment of FIGS. 1–5.

The head support 10b shown in FIG. 13 also resembles the embodiment of FIGS. 1–5 with respect to nape-engagement means 12b and forehead-engagement means 14b; here, however, adjustable shoulder-engagement means 210 is illustrated replacing the chest-engagement means of above-described embodiments.

Figure 4:
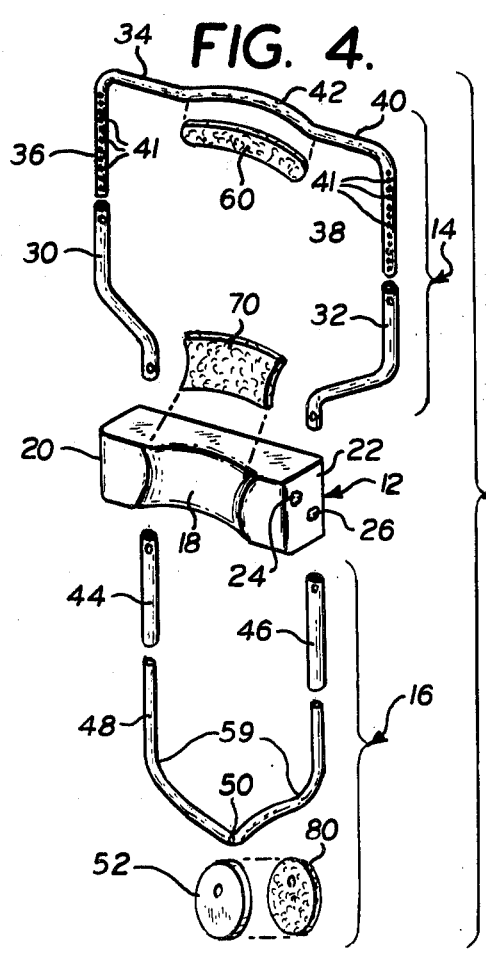
FIG. 4 is an exploded isonetric view of the principal components of the device shown in FIGS. 1-3.
Figure 5:
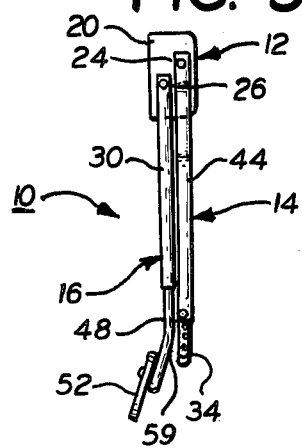
FIG. 5 is a side view of the device of FIG. 1 shown in assembled but collapsed position for carrying.

Another concept is the use of padding at points of body contact--pad 60 at forehead-engaging area 42, pad 70 at nape-engaging area 18, and pad 80 on chest-engaging element 52 (see FIG. 4). Any one or all of these pads may be affixed to the head support either for prolonged use or, when the head-support is to be worn by different people, as detachable, replaceable "throw-away" elements. Attachment by conventional methods, such as pressure-sensitive adhesive or Velcro fasteners, may be readily accomplished.

It is evident that the features of bridge-of-the-nose engagement, shoulder engagement, single pivot and padding points of body contact may be incorporated into any of the embodiments herein described, where applicable.

A further concept is here disclosed wherein any of the head supports described above may be combined with a sound-producing device, such as a radio or cassette tape player, incorporated into or attached to the structure of the head support. Accompanying earphones or earplug would provide the head support wearer with a source of relaxing, or even sleep-inducing, sound.

There have been described in the foregoing, in full, clear, concise and exact terms, the best embodiments of the invention presently contemplated. It is understood, however, that various modifications and combinations may be made of these embodiments without departing from the spirit or essence of this invention.

I claim:

1. A head support, comprising:
   nape-engagement means for positioning in such manner as to engage the nape of the neck of the wearer;
   forehead-engagement means for positioning around the wearer's forehead; and
   chest-engagement means for placement on the wearer's chest,
   said nape-engagement means, said forehead-engagement means and said chest-engagement means being so interconnected that said nape-engagement means acts as a force-transmitting fulcrum through which the forward and downward pressure of the wearer's head applied to said forehead-engagement means is passed on to said chest-engagement means.

2. A head support as in claim 1, wherein said forehead-engagement means is pivotally connected to said nape-engagement means, and comprises adjustment means for setting the length of said forehead-engagement means to fit the wearer's head.

3. A head support as in claim 1, wherein said forehead-engagement means is held in desired angular position in fitting engagement with the forehead by retention means between said nape-engagement means and said forehead-engagement means.

4. A head support as in claim 1, wherein said chest-engagement means comprises adjustment means for adapting the length of said chest-engagement means so as to fit different depths of chests.

5. A head support as in claim 1, wherein said chest-engagement means is held in desired angular position upon the chest by retention means between said nape-engagement means and said chest-engagement means.

6. A head support as in claim 1, wherein said nape-engagement means further comprises an occipital support means for engaging and retaining the rear head portion of the wearer in an upright position.

7. A head support as in claim 6, wherein said nape-engagement means further comprises a posterior support means adapted to engage the upper portion of the wearer's back.

8. A head support as in claim 7, wherein said nape-engagement means further comprises a shoulder-engaging-frame means extending anteriorly from said posterior support means and adapted to fit over the wearer's shoulders.

9. A head support as in claim 1, wherein said chest-engagement means further comprises a chin-support means extending upwardly to beneath the wearer's chin.

10. A head support as in claim 8, wherein said nape-engagement means further comprises lateral support means extending upwardly from said shoulder-engaging-frame means for engaging and supporting the side portions of the wearer's neck and head.

11. A head support as in claim 1, wherein said nape-engagement means and said chest-engagement means are of a single integral construction.

12. A head support as in claim 11, wherein said integral construction is a double-walled shell-defining air chamber means, and wherein said head support further comprises inflating means coupled to said air chamber means, so that said double-walled means, when inflated, forms a semi-rigid enclosure.

13. A head support as in claim 12, wherein said chest-engagement means comprises a slit portion, and fastening means on either side thereof to permit putting on, taking off, and positioning said support around the wearer's head.

14. A head support as in claim 4, wherein said chest-engagement means comprises a U-shaped member which extends above the wearer's chest and which is connected to said adjustment means for adapting the length of said chest-engagement means; and a chest-engaging element which depends from said U-shaped member and which is adapted to be placed in fitting engagement against the chest of the wearer.

15. A head support as in claim 1, wherein the body-contacting portion of at least one of said nape-engagement means, said forehead-engagement means and said chest-engagement means is provided with replaceable padding means.

16. A head support, comprising:
    nape-engagement means for positioning in such manner as to engage the nape of the neck of the wearer;
    bridge-of-the-nose-engagement means for positioning on the bridge of the nose of the wearer; and
    chest-engagement means for placement on the wearer's chest,
    said nape-engagement means, said bridge-of-the-nose-engagement means and said chest-engagement means being so interconnected that said nape-engagement means acts as a force-transmitting fulcrum through which the forward and downward pressure of the wearer's head applied to said bridge-of-the-nose-engagement means is passed on to said chest-engagement means.

17. A head support, comprising:
    nape-engagement means for positioning in such manner as to engage the nape of the neck of the wearer;
    forehead-engagement means for positioning around the wearer's forehead; and
    shoulder-engagement means for placement on the wearer's shoulders,
    said nape-engagement means, said forehead-engagement means and said shoulder-engagement means being so interconnected that said nape-engagement means acts as a force-transmitting fulcrum through which the forward and downward pressure of the wearer's head applied to said forehead-engagement means is passed on to said shoulder-engagement means.

18. A head support, comprising:
    nape-engagement means for positioning in such manner as to engage the nape of the neck of the wearer;
    bridge-of-the-nose-engagement means for positioning on the bridge of the nose of the wearer; and
    shoulder-engagement means for placement on the wearer's shoulders,
    said nape-engagement means, said bridge-of-the-nose-engagement means and said shoulder-engagement means being so interconnected that said nape-engagement means acts as a force-transmitting fulcrum through which the forward and downward pressure of the wearer's head applied to said bridge-of-the-nose-engagement means is passed on to said shoulder-engagement means.

* * * * *